(12) United States Patent
Schoeppe et al.

(10) Patent No.: US 9,468,896 B2
(45) Date of Patent: Oct. 18, 2016

(54) PHOSPHOLIPID-CONTAINING EMULSIFIER COMPOSITION

(71) Applicant: Cargill, Incorporated, Wayzata, MN (US)

(72) Inventors: Arnulf Schoeppe, Hamburg (DE); Daniel Steiger, Pinneberg (DE); Susanne Tirok, Hamburg (DE)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 14/437,669

(22) PCT Filed: Oct. 24, 2013

(86) PCT No.: PCT/US2013/066604
§ 371 (c)(1),
(2) Date: Apr. 22, 2015

(87) PCT Pub. No.: WO2014/066632
PCT Pub. Date: May 1, 2014

(65) Prior Publication Data
US 2015/0298084 A1    Oct. 22, 2015

(30) Foreign Application Priority Data
Oct. 24, 2012    (EP) .................................... 12007324

(51) Int. Cl.
| B01F 17/00 | (2006.01) |
| A21D 2/32 | (2006.01) |
| A23J 7/00 | (2006.01) |
| A23L 1/035 | (2006.01) |
| A23L 1/24 | (2006.01) |
| A23D 7/01 | (2006.01) |
| C11B 11/00 | (2006.01) |
| A23G 3/40 | (2006.01) |
| A61K 8/55 | (2006.01) |
| A61K 47/24 | (2006.01) |

(52) U.S. Cl.
CPC .............. *B01F 17/0092* (2013.01); *A21D 2/32* (2013.01); *A23D 7/011* (2013.01); *A23D 7/013* (2013.01); *A23G 3/40* (2013.01); *A23J 7/00* (2013.01); *A23K 20/158* (2016.05); *A23L 1/035* (2013.01); *A23L 1/24* (2013.01); *A61K 8/553* (2013.01); *A61K 47/24* (2013.01); *C11B 11/00* (2013.01); *A61K 2800/10* (2013.01)

(58) Field of Classification Search
None
See application file for complete search history.

(56) References Cited

U.S. PATENT DOCUMENTS 5,120,561 A    6/1992    Silva et al.

FOREIGN PATENT DOCUMENTS

| DE | 2715286 A1 | 10/1978 |
| EP | 0604806 A2 | 7/1994 |
| GB | 0090454 A1 | 10/1983 |

*Primary Examiner* — Samantha Shterengarts

(57) ABSTRACT

The present invention relates to a novel phospholipid emulsifier composition allowing stabilizing water-in-oil emulsions, and to a novel process for the preparation of such emulsions involving a counter-current extraction process involving a plurality of mixing and separation stages for fractionating a phospholipid-containing feed material into two or more fractions enriched in one or more phospholipids.

17 Claims, 2 Drawing Sheets

PHOSPHOLIPID-CONTAINING EMULSIFIER COMPOSITION

CROSS-REFERENCE TO RELATED APPLICATION

This application is a national phase application of International Application PCT/US2013/066604, Filed 24 Oct. 2013, entitled PHOSPHOLIPID-CONTAINING EMULSIFIER COMPOSITION, which claims the benefit of European Application No. 12007324.2, Filed 24 Oct. 2012, entitled, which is hereby incorporated by reference in its entirety PHOSPHOLIPID-CONTAINING EMULSIFIER COMPOSITION.

FIELD OF THE INVENTION

The subject invention relates to a novel phospholipid comprising emulsifier, to a process for extracting and separating phospholipids from phospholipid-containing materials to obtain the emulsifier composition, and to its various uses.

BACKGROUND OF THE INVENTION

Water-in-oil emulsions are dispersions of water droplets in an oil/lipid continuous phase. Margarine and butter for example are formed by this type of emulsion. Additionally water in oil emulsions can be employed to form multiple emulsions of water-in-oil-in water (w/o/w) where a primary emulsion is dispersed in a secondary aqueous phase.

These are typically used to produce fat reduced food products but also to encapsulate water soluble substances. Presently, mainly synthetic emulsifiers are able to form stable water in oil emulsions and these have been used successfully in research.

However, the use of such synthetic emulsifiers is limited by food regulations, and food manufacturers are hence reluctant to use these.

It would therefore be highly desirable to be able to use a naturally derived emulsifier composition that allows to work under present food regulations.

SUMMARY OF THE INVENTION

Accordingly, in a first aspect, the present invention relates to a Phospholipid emulsifier composition comprising Phosphatidyl Choline (PC), Lyso Phosphatidyl Choline (LPC), Phosphatidyl Inositol (PI), Phosphatidyl Ethanolamine (PE) and Phosphatidic Acid (PA), wherein the emulsifier has a phospholipid ratio $R_1:R_2$ in the range of from 1:1 to 1.7:1, wherein $R_1$ is defined as the weight ratio of phospholipid components according to general formula I:

$$R_1 = \frac{PC + LPC + PI + PA}{PE}, \quad \text{(I)}$$

and wherein $R_2$ is defined as the weight ratio of phospholipid components according to general formula II:

$$R_2 = \frac{PC + LPC + PI}{PE + PA}. \quad \text{(II)}$$

In a second aspect, the present invention relates to a water-in-oil emulsion comprising the emulsifier according to the invention. In a third aspect, the present invention also relates to a water-in-oil-in-water emulsion comprising the above emulsions.

In yet a further aspect, the present invention relates to an extraction process involving a plurality of mixing and separation stages for fractionating a phospholipid-containing feed material into two or more fractions enriched in one or more phospholipids, comprising the following steps:

(a) contacting the phospholipid-containing starting material under agitation with an extractant comprising an aliphatic alcohol selected from $C_1$ to $C_3$ alcohols and mixtures thereof for a period of time sufficient to effectuate the transfer of at least a fraction of the phospholipids into the extractant;

(b) separating the obtained mixture into a phospholipid-enriched extract from a residual raffinate by a process comprising applying centrifugal forces, wherein the phospholipid-enriched extract from each separation stage is at least in part returned to the previous, or further upstream mixing stages, and wherein a final phospholipid-enriched extract is separated from a first residual raffinate.

In again a further aspect, the subject invention relates to a phospholipid emulsifier obtainable according to the process according to the invention. In a further aspect, the subject invention relates to the use of the phospholipid-enriched extract or a phospholipid-depleted raffinate for food products, preferably bakery products, nutraceutical compostions, confectionery, convenience foods, margarines, spreads; animal feed products and/or pharmaceuticals compositions, or as release agents or industrial emulsifiers.

BRIEF DESCRIPTION OF THE FIGURES

These and further features can be gathered from the claims, description and drawings and the individual features, both alone and in the form of sub-combinations, can be realized in an embodiment of the invention and in other fields and can represent advantageous, independently protectable constructions for which protection is hereby claimed. Embodiments of the invention are described in greater detail hereinafter relative to the drawings, wherein:

DETAILED DESCRIPTION OF THE INVENTION

Figure 1:
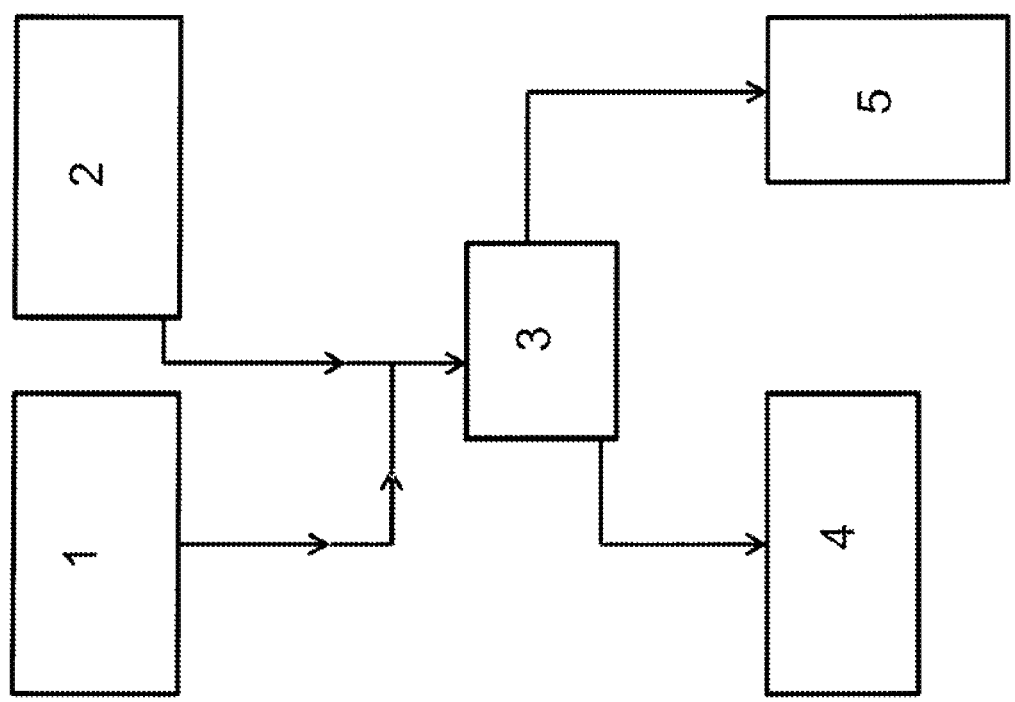
FIG. 1 discloses a schematic diagram of a preferred embodiment of the fractionation process, including peripheral apparatus, as employed in the experiments.

Phospholipids are important components of cell membranes of plants, microbes and animals. The term "phospholipid", refers to compounds derived from fatty acids and a phosphate-containing compound attached to glycerol or the amino alcohol sphingosine, resulting in compounds with fat-soluble and water-soluble regions. The term "lecithin" herein is used for mixtures of phospholipids and triglycerides. The main glycerol-containing phospholipids in lecithin are phosphatidyl choline, phosphatidyl inositol, phosphatidyl ethanolamine and phosphatidic acid, further referred to herein as PC, PI, PE, and PA, respectively. The actual composition of phospholipids depends on the source. A further term employed for highly polar components of lecithin are acetone insolubles, further referred to as AI herein. These are lecithin components that are generally insoluble in phospholipid-saturated acetone, which is typically employed to remove neutral triglycerides from crude lecithin.

The emulsifier composition according to present invention preferably has a phospholipid $R_1$ value in the range of from 1.2 to 2.6, preferably in the range from 1.9 to 2.6, more preferably in the range from 2.0 to 2.4.

The emulsifier composition according to present invention preferably has a phospholipid $R_2$ value in the range of from 0.6 to 1.6, preferably in the range from 0.8 to 1.6, more preferably 1.0 to 1.5.

The two values indicate a high emulsifying capacity, with good interfacial layer stabilising properties.

The emulsifier composition according to the invention preferably has an acetone insoluble content of at least 60 weight %, more preferably at least 61, yet more preferably at least 65, and most preferably at least 69 weight %.

It preferably has a phosphatidyl choline content of at most 20 weight %, preferably at most 12 weight %, more preferably at most 10 weight %, yet more preferably at most 8 weight % and most preferably at most 5 weight %.

The present process further relates to a water-in-oil emulsion comprising the emulsifier according to the invention. It further preferably relates also to a secondary, water-in-oil-in-water emulsion comprising the primary water-in-oil emulsion.

The emulsions according to the present invention preferably comprise of from 1 to about 99% by weight of a lipid, and of from 1 to 99% by weight of one or more aqueous phases, and from more than 0 to about 10% by weight, preferably of 0.001 to 5% by weight, more preferably of from 0.01 to 3% by weight, from of the specific phospholipid emulsifier composition according to the invention, based on the amount of lipid utilized.

The present invention also preferably relates to a process for the preparation of an water-in-oil emulsion, comprising (i) contacting an lipid composition with a suitable amount of an emulsifier according to the invention, to obtain an emulsion stabilized lipid composition, and (ii) contacting the emulsion stabilized lipid composition with an first aqueous phase to form a water-in-oil emulsion. The thus obtained water-in-oil emulsion may advantageously be employed in a process further comprising dispersing the water-in oil emulsion in a second aqueous phase to obtain an oil-in-water-in oil emulsion. This second external aqueous phase typically contains one or more second hydrophilic emulsifier compositions.

Any vegetable or animal derived oil, which may be solid or liquid at ambient temperature, can be used as lipid component in the present emulsions. Suitable vegetable oils for use include, for example, soybean oil, sunflower oil, rapeseed oil, cottonseed oil, olive oil, corn oil, ground nut or peanut oil, safflower oil, linola oil, linseed oil, palm oil, shea butter, marine oils, biomass oils derived from other sources than those mentioned herein, and/or coconut oil, all of which may be partially or completely hydrogenated or modified otherwise, and mixtures thereof. Particularly useful are soybean oil and partially hydrogenated soybean oil. Suitable oils of animal origin for use include, for example, butter fat and fish oil.

Suitable sources of marine oils include oils derived from marine life forms such as microalgae or cyanobacteria.

Mineral oils and derivatives thereof, may also be used.

Any suitable aqueous phase may be used. This includes water, any dilute or concentrated aqueous solution that may contain any solute, and a mixture. Preferred for use is water.

The emulsions of the present invention may be prepared by any known technique. The preparation of the primary and/or secondary emulsion may advantageously be performed by a conventional mixing apparatus, or preferably by passing the stabilized lipid phase or the primary emulsions through a membrane with suitably small pores into the first aqueous phase. This is in particular useful for secondary emulsions, whereby a more homogenous particle size is achieved which typically increases emulsion stability.

In a preferred embodiment, the w-o-w emulsions according to the subject invention are formed by a process for membrane emulsification, comprising circulating the secondary aqueous phase through a typically tubular vessel comprising a lumen, and a membrane surrounding the lumen, whereby the membrane has pores of defined width and suitable size, e.g. at an average pore width in the range of from 5 µm to 15 µm, preferably of 10 µm. The outer membrane wall is immersed in the primary emulsion, which is pressured into the lumen and into the flowing secondary phase through the pores in the membrane at a predetermined rate, thereby forming the secondary emulsion.

This process also permits to create emulsions with a high concentration of particles, in particular if the secondary phase is recycled through the membrane vessel.

Preferably, the emulsion according to the invention further comprises one or more viscosity modifiers. Suitable viscosity modifiers include polysaccharides including starches, microbial gums, agar agar, pectin, alginic acid, sodium alginate, beta-glucans, carrageenan, glucomannan, guar gum, gum ghatti, gum tragacanth, karaya gum, tara gum, fenugreek gum and/or locust bean gum. The term "microbial gums", herein refers to all gum polysaccharides of microbial origin, i.e. from algae, bacteria or fungi.

Examples thereof include, for instance, gellan and xanthan gums produced by bacteria. A preferred microbial gum for use herein is xanthan gum, a microbial desiccation resistant polymer prepared commercially by aerobic submerged fermentation. Xanthan is an anionic polyelectrolyte with a β-(1,4)-D-glucopyranose glucan backbone having side chains of (3,1)-α-linked D-mannopyranose-(2,1)-p-D-glucuronic acid-(4,1)-p-D-mannopyranose on alternating residues.

Agar agar is a plant-derived gum polysaccharide. The gelling agent is an unbranched polysaccharide obtained from the cell walls of some species of red algae, primarily from the genera *Gelidium* and *Gracilaria*, or seaweed.

Another suitable viscosity modifier is pectin, which is a heterogenous group of acidic polysaccharides found in fruit and vegetables and mainly prepared from waste citrus peel and apple pomace.

Pectin has a complex structure, wherein a large part of the structure consists of homopolymeric partially methylated poly-α-(1,4)-D-galacturonic acid residues with substantial hairy non-gelling areas of alternating α-(1,2)-L-rhamnosyl-α-(1,4)-D-galacturonosyl sections containing branch points with mostly neutral side chains of 1 to 20 residues, of mainly L-arabinose and D-galactose. The properties of pectins depend on the degree of esterification, which is normally about 70%.

Alginic acid and sodium alginate are vegetable gums of linear polymers containing β-(1,4)-linked D-mannuronic acid and α-(1,4)-linked L-guluronic acid residues produced by seaweeds. Beta-glucans which are defined to consist of linear unbranched polysaccharides of linked β-(1,3)-D-glucopyranose units in a random order. Beta-glucans occur, for example, in the bran of grains, such as barley, oats, rye and wheat.

Carrageenan is a generic term for polysaccharides prepared by alkaline extraction from red seaweed. Carrageenan includes linear polymers of about 25,000 galactose derivatives. The basic structure of carrageenan consists of alternating 3-linked β-D-galactopyranose and 4-linked α-D-galactopyranose units.

Guar gum, which is defined as a galactomannan consisting of a α-(1,4)-linked β-D-mannopyranose backbone with branch points from their 6-positions linked to α-D-galactose. It is non-ionic and typically made up of about 10,000 residues. Guar gum is highly water-soluble and, for example, more soluble than locust bean gum.

Gum ghatti is a natural gum obtained from Indian tree, *Anogeissus latifolia.*

Gum tragacanth is a viscous, odourless, tasteless, water-soluble mixture of polysaccharides obtained from sap which is drained from the root of several species of Middle Eastern legumes of the genus *Astragalus*, including *A. adscendens, A. gummifer*, and *A. tragacanthus.*

Karaya gum, is a vegetable gum produced as an exudate by trees of the genus *Sterculia*. It is an acid polysaccharide composed of the sugars galactose, rhamnose and galacturonic acid.

Tara gum is a white or beige, nearly odourless powder that is produced by separating and grinding the endosperm of *C. spinosa* seeds. The major component of the gum is a galactomannan polymer similar to the main components of guar and locust bean gums.

Fenugreek gum, consists of D-mannopyranose and D-galactopyranose residues with a molar ratio of 1.2:1.0. The main chain of this galactomannan comprises β-(1,4)-linked D-mannopyranose residues, in which 83.3% of the main chain is substituted at C-6 with a single residue of α-(1,6)-D-galactopyranose. The galactomannan is made up of about 2,000 residues. Fenugreek gum seed endosperm, contains 73.6% galactomannan.

Locust bean gum is a galactomannan similar to guar gum. It is polydisperse, non-ionic, and is made up of about 2,000 residues. Locust bean gum is less soluble and less viscous than guar gum and is soluble in hot water.

Finally, starches may be employed including pregelatinized starches. These are known to the skilled person and can be manufactured by any method from the art. Porous starch or maltodextrins are preferably obtained by enzymatic treatment; e.g. granular starch treated with amylolytic enzymes, such as alpha-amylases and glucoamylases. Suitable sources to produce such porous starch to be employed in the present process include wheat, maize, pea, potato, barley, tapioca, rice, sago or sorghum and mixtures thereof. Preferably the source is rice, barley, maize or tapioca and mixtures thereof. More preferably, the source is waxy maize starch or regular corn starch and mixtures thereof.

Preferably the viscosity modifier comprises xanthan gum and/or locust bean gum. The viscosity modifier may be present in an amount of 1% weight to 10% weight, based on the dry matter of the composition.

The primary and/or secondary emulsion may further comprise a salt of a polyvalent metal, preferably bivalent, more preferably an alkaline-earth metal salt. Yet more preferably, the metal is calcium, and most preferably, the salt is calcium carbonate or calcium chloride. The presence of calcium salts was found to increase the stability of the emulsions further.

The emulsifier compositions according to the present invention are preferably obtainable by a counter-current extraction process.

In step (a) of this process, a phospholipid-containing starting material is coctacted under agitation with an extractant comprising an aliphatic alcohol selected from $C_1$ to $C_3$ alcohols and mixtures thereof, preferably ethanol, for a period of time sufficient to effectuate the transfer of at least a fraction of the phospholipids into the extractant.

In process step (b), the mixture obtained in step (a) is separated by a process involving centrifugal forces.

The term "centrifugal forces" herein refers to the apparent outward force that draws a rotating body away from the centre of rotation. The process preferably is a mechanical process, more preferably by applying the centrifugal force in a rotating device, such as a centrifuge.

Figure 2:
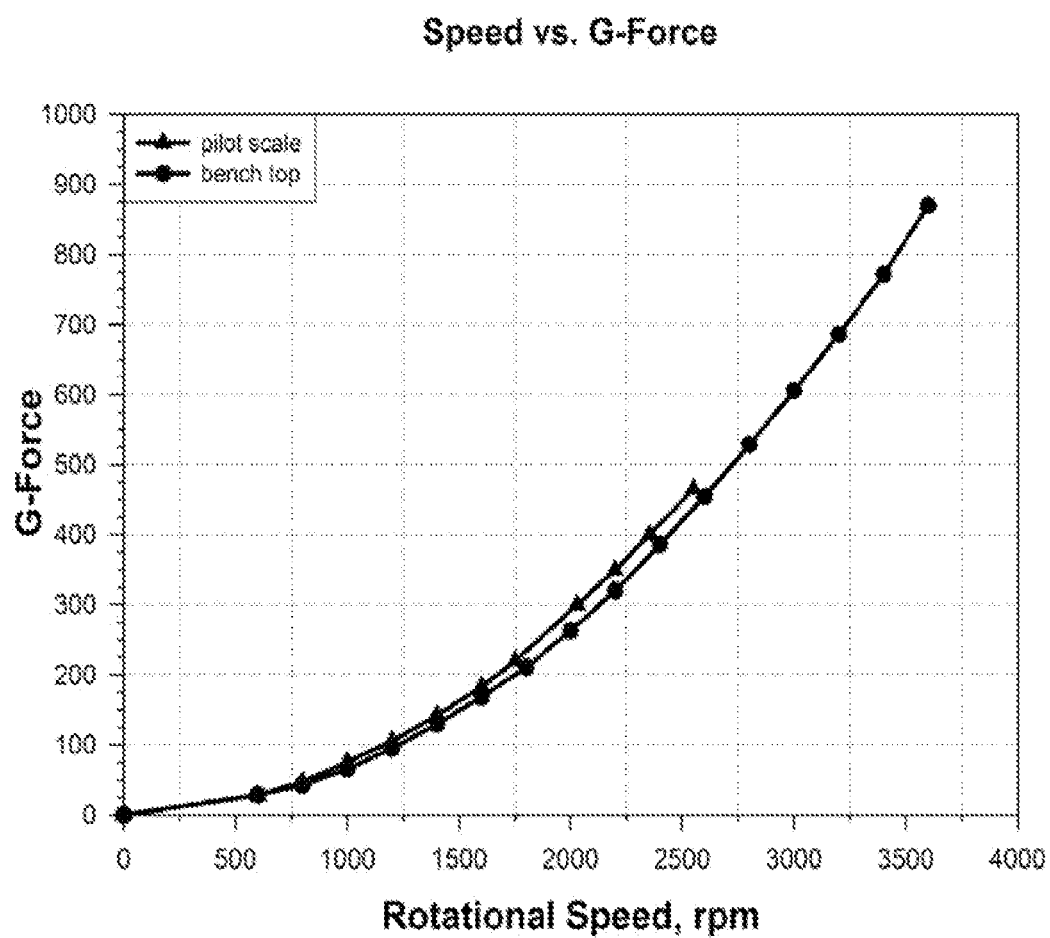
FIG. 2 discloses the ratio of rotation speed versus G-forces applied to mixtures according to a preferred embodiment of the subject process; two different rotors were employed in a centrifugal separator; the X-axis denotes the rotations, as rotations per minute, the Y-axis the G-force.

The term "mixture" herein refers to any mixture that is obtained in any of the stages of the present extraction process, and includes emulsions and dispersions, and inhomogeneous mixtures and blends. The separation process is preferably executed in a centrifugal device, at a Relative Centrifugal Force (RCF) in the range of from 2 to 25.000 G, more preferably of from 10 to 20.000 G, yet more preferably of from 100 to 18.000 G, and yet more preferably of from 400 to 15.000 G. Since the RCF is positively related with the rotor radius and the rotation speed of a centrifuge, the rotation speed required for a given rotor radius may conveniently be calculated by a skilled artisan. FIG. 2 shows the Relative Centrifugal Force applied for a preferential embodiment of the subject process, whereby a suitable centrifugal device was employed.

In the present process, the phospholipid-containing starting material is preferably contacted in (a) with the extractant in a co-current or counter-current mixing operation. While the contact may be co- or counter-current, depending on the manner and apparatus wherein the two liquids are mixed, the overall process flow is counter-current, i.e. the phospholipid-containing starting material is contacted in a first stage with the extractant from a second or further stage, and so on.

Preferably, the water concentration in the aliphatic alcohol is in the range of from 0 to 10%, preferably from 0 to 5% by weight.

The extracted phospholipids preferably comprise one or more of phosphatidyl choline (PC), LPC, phosphatidyl ethanolamine (PE), phosphatidyl inositol (PI) and/or phosphatidic acid (PA). The exact composition of the extracted and residual components largely depends on the starting material, the extractant, and the conditions under which the starting material is extracted, but also the chemical nature of the extractant, and the composition of the extractant phase, e.g. water content and pH value.

The process preferably results in an emulsifying composition—as the final raffinate phase—comprising less than 20% by weight of phosphatidyl choline (PC), more preferably less than 15% by weight, yet more preferably less than 12% by weight.

More preferably, the final raffinate phase comprises phosphatidyl choline (PC) in an amount in the range of from 1 to 10% by weight, more preferably of from 2 to 9% by weight, and yet more preferably of from 3 to 8% by weight.

The final raffinate phase preferably has an Acetone Insoluble content of from 55 to 75% by weight, more preferably of from 60 to 70% by weight, yet more preferably of from 65 to 70% by weight.

Preferably, steps (a) and (b) are executed at least in part in a multistage extraction apparatus comprising for each stage: i) a rotor, ii) a mixing chamber connected to the rotor, and wherein the two liquid streams are mixed, and wherein the mixing chamber comprises iia) a stationary agitator placed in the mixing chamber, and iib) a settling chamber in which the liquid streams are separated by the centrifugal force generated by the mixing chamber.

Advantageously, the stationary agitator comprises a stationary disc, and the mixing is achieved through the speed differential between the stationary disc and the rotating mixing chamber. In step (c), a raffinate fraction is isolated as the emulsifier composition.

The present invention further preferably relates to the step of incorporating the emulsifier into a product as described herein above.

DETAILED DESCRIPTION OF THE DRAWING

FIG. 1 depicts a preferred embodiment of the subject process. Herein, a phospholipid feed tank (1) and an extractant tank (2) comprising a heat exchanger (not depicted) are fluidly connected to a multistage centrifugal liquid-liquid extractor (3) having a final extractant outlet (4) and a final raffinate outlet (4). The extractant feed is entered countercurrent to the phospholipid feed into the extractor (3), and the final extractant is collected in an extractant vessel (5) and a raffinate vessel (6). Both tanks (1) and (2) are supplied with flow meters to adjust and control the flow needed for the actual experiment and thus the extraction ratio. Temperature control equipment is installed at the heat exchanger and at both centrifugal extractor inlets and outlets.

Unadjusted lecithin and Ethanol adjusted to and water content from 0% to 10% by weight are filled into the tanks (1) and (2), respectively. The Extractant temperature may be adjusted by circulating through the heat exchanger.

In the process according to the subject invention, preferably the final extract obtained from the extractant phase comprises at least 25% by weight of phosphatidyl choline (PC), and more than 50% by weight of Acetone Insolubles (AI).

The present process employs a multistage process, i.e. comprising repeated extraction steps, and hence results in a higher yield of desired phospholipids in the extract phase, while simultaneously producing a raffinate phase having a composition significantly different from those typically obtained in the processes disclosed in the prior at.

The phospholipid-containing starting material may be any suitable material, such as crude lecithin of plant or animal origin, oil-derived gums and/or dried gums as obtainable from plant or animal oil and/or fat in degumming processes. Typically, the phospholipid composition of the starting material is in part influenced by the preparation method, however largely defined by the origin of the material.

Suitable lecithin compositions have been disclosed in detail in Kirk-Othmer, Food and Feed Technology, 5$^{th}$ Edition, Volume 1, 2007, John Wiley & Sons.

The phospholipid-containing material preferably comprises one or more phospholipids selected from the group consisting of unmodified or chemically modified forms of phosphatidyl choline (PC), Lyso phosphatidyl choline (LPC), phosphatidyl ethanolamine (PE), Nacylphosphatidyl ethanolamine (NAPE), phosphatidyl serine (PS), phosphatidyl inositol (PI), phosphatidyl glycerol (PG), diphosphatidyl glycerol (DPG), phosphatidic acid (PA), plasmalogen, lecithin and vegetable oil-derived gums. Of these, of phosphatidyl choline (PC), phosphatidyl ethanolamine (PE), and phosphatidyl inositol (PI) typically form the majority of the components.

The phospholipid-containing material for use in the subject process may comprise triglyceride oil, or is may be partially or completely de-oiled, for instance by acetone or hexane extraction, as disclosed in DE-A-1234680. The presence of the triglycerides was found to not be detrimental for the subject process, since the triglycerides were found hardly soluble in the alcohol extractant employed. Hence the present process advantageously permits the use of crude phospholipid compositions as starting component. Moreover, the presence of triglycerides in the starting material may reduce the viscosity, and hence may reduce the energy required to achieve a suitable mixing of the extractant phase and the raffinate phase.

Furthermore, addition of oil may advantageously be reduced to the raffinate fraction, thereby reducing the overall volume subjected to the de-oiling step.

Preferred due to the wide availability is plant oil derived lecithin, selected from the group consisting of soybean lecithin, corn germ oil lecithin, rapeseed lecithin including lecithin derived from canola, field mustard and other rape seed variants and hybrids, rice oil lecithin, sunflower lecithin, cotton seed lecithin, peanut lecithin, palm oil lecithin, marine oil lecithin, biomass lecithin, and mixtures thereof. Alternatively, animal-based lecithin may be employed, including egg yolk lecithin, milk lecithin and/or brain lecithin, and or mixtures thereof. The raw material to be fractionated is preferably chosen in function of the fraction or fractions required. If a phospholipid fraction that is virtually free from linolenic acid moieties is desired, sunflower lecithin, cottonseed lecithin or corn germ oil lecithin may advantageously be used. For applications requiring a fraction with not too high in unsaturated fatty acid residues, and hence enhanced oxidative stability, rapeseed lecithin may preferably be employed as starting material. Soybean lecithin is strongly preferred due to the availability and its high PC content.

If a phospholipid-comprising mixture, which may further comprise triglycerides and other components normally associated with its isolation and/or preparation, is blended with an aliphatic alcohol under agitation, typically a two-phase system is formed, which upon on settling yields an alcohol-containing, lighter, upper layer containing some phospholipids and possibly triglycerides and other alcohol soluble components, and a phospholipid-containing lower layer containing the remainder of the triglycerides, along with some alcohol.

The standard methods of analysis for the components disclosed herein are according to the European Council Directive No 95/2/EC of 20 Feb. 1995 on food additives other than colours and sweeteners.

While settler/mixer units may be employed to separate extractant and raffinate phases, the separation due to normal gravity is slow, and requires careful control of the temperatures of the liquids. Yet further, the heavier phase tends to have a comparatively high viscosity, making the separation difficult, and leading to a loss in extract yield.

Applicants have now found that if the density separation at each stage is enhanced by increasing the gravitational forces by using one or more centrifugal extractors, while also increasing the energy put into emulsifying the phospholipid phase, the extraction yield of the described phospholipids may be strongly increased, while at the same time the time required to perform the extraction and phase separation is strongly reduced.

Moreover, the thus obtained lighter extracted fraction and the heavier raffinate fraction were found to have different compositions from those typically obtained in the extraction process using mixer/settler units, thereby enhancing the potential for different uses.

Applicants have further found the distribution of the various components over both phases is primarily governed by the phospholipid-containing material; phospholipid-containing material to extractant ratio, the phospholipid composition, the temperature and the extractant composition, especially its water content and/or the acid value, as well as the mechanical agitations supplied to form the liquid/liquid emulsion.

The multi-component system makes a selective fractionation difficult, since the extraction of the different components of the starting material may change when the different parameters are varied. In general, the extractant phase contains more phospholipids at elevated temperatures, at reduced water content.

The present process preferably employs a multistage mixing and liquid/liquid separation apparatus or device. The process according to the invention may be carried out as a batch process, but preferably is executed in a continuous operation. Additionally to centrifugal devices employed, also mixer/settler systems may advantageously be used.

In the liquid-liquid two-phase extraction process according to the invention, extractant and material to be extracted are introduced into a multistage extraction apparatus. The multistage extraction apparatus preferably has a first inlet and a second inlet. The introduction of both liquids is preferably performed in a counter-current direction to each other, i.e. the lighter phase may advantageously be introduced at the top of the multistage separation device, in the first inlet, while the phospholipid-containing material may advantageously be introduced at the bottom, i.e. the second inlet.

In each stage, preferably a mixture of the feed to be extracted and of the extractant preferably may be cycled through a mixer and an overflow vessel, and a quantity of the mixture of solvent and substance may be withdrawn from the overflow vessel at each stage, and separated in a centrifuge into extract and raffinate.

The raffinate is then preferably introduced into the following extraction stage or moved to a further processing step from the final stage, whereas the extract is returned to a preceding stage, or discharged from the first stage into a further processing step. Accordingly, the present process preferably comprises introducing a feed comprising the phospholipid-containing material into a multistage extraction apparatus in a first direction; introducing an extractant comprising an aliphatic alcohol selected from $C_1$ to $C_3$ alcohols and mixtures thereof, which extractant flows through the multistage extraction apparatus in a second direction and forms an extract phase of the fractionation process; contacting the feed and the extractant under agitation; wherein the second direction is counter-current to the first direction.

A particularly suitable multistage extraction apparatus comprises for each stage i) a rotor, ii) a mixing chamber connected to the rotor, and wherein the two liquid streams are mixed, and wherein the mixing chamber comprises iia) a stationary agitator placed in the mixing chamber, and iib) a settling chamber in which the liquid streams are separated by the centrifugal force generated by the mixing chamber. The stationary agitator preferably comprises a stationary disc, and wherein the mixing is achieved through the speed differential between the stationary disc and the rotating mixing chamber. The disc may also act as a pump, thereby moving the extract and raffinate phases through the multistage apparatus.

The emulsifier isolated from the raffinate was found to comprise a different composition of phospholipids to a raffinate obtained in other known processes, and may thus be useful for different purposes, including food products, more preferably bakery products, nutraceuticals, confectionery, convenience foods, margarines, spreads; nutraceuticals and pharmaceuticals. Alternative preferred uses include cosmetics; animal feed products and/or pharmaceuticals compositions, or as release agents or industrial emulsifiers.

Accordingly the subject invention also relates to the use of the emulsifier for food products, preferably bakery products, nutraceuticals, confectionery, convenience foods, margarines, spreads; animal feed products and/or pharmaceuticals compositions, or as release agents or industrial emulsifiers.

The extractant comprising the aliphatic alcohol flows through the multistage extraction apparatus in a first direction and contributes to the extractant phase. The material to be extracted flows through the multistage extraction apparatus in a second direction, which second direction is counter-current to the first direction, and contributes to a raffinate phase of the two-phase extraction process.

The two phases are contacted directly, under agitation, to transfer extractable components from the feed into the extractant phase, resulting in an increasingly enriched extractant phase, and an increasingly depleted raffinate phase.

The following, non-limiting examples illustrate the process according to the invention and to assist one of ordinary skill in making and using the same. The examples are not intended in any way to otherwise limit the scope of the invention.

Experimental Part

Extractor:

A multistage centrifugal liquid-liquid extractor obtained from Rousselet Robatel (France) was employed in the experiments. The extractor comprised 6 rotating bowls, connected to a central rotor, with a maximum rotation speed of 2.900 rpm, and a maximum flow rate (2 phases) of 25 to 30 l/h. The bowls had a useful volume of 0.39 l.

The peripheral equipment was employed according to the schema depicted in FIG. 1. Lecithin and Ethanol were adjusted in their respective water contents, and filled into feed tanks. The temperature of the ethanol feed was adjusted by circulating it through a heat exchanger, while the temperatures in the process stages were controlled at the heat exchanger and at both centrifugal extractor inlets and outlets. Both lecithin and ethanol tank were supplied with flow meters to adjust and control the flow needed for the actual experiment and thus the extraction ratio.

At start up, the ethanol flow was adjusted first, and a rotation speed was set. Then the lecithin flow was adjusted.

The system was allowed to stabilize for about 5 min of continuous extract and raffinate outlet flow, and then the actual flows were determined by collecting extract and raffinate phase coming out of the extractor during 5 min and determining weight of the total amount. 5 l of each fraction were collected for further analysis.

Yield Determination:

For yield calculation extract and raffinate streams were collected during 5 minutes and weighed. From that the throughput in kg/h was calculated. Since the extract phase still contained a certain amount of raffinate phase, the raffinate phase content was determined as follows:

A defined amount of well homogenised extract phase was weighed into a centrifuge flask of known weight and centrifuged at 5000 rpm for 10 min (10 C.°). Then the supernatant extract phase was carefully decanted and sediment weighed as raffinate of the homogenized extract phase. The corrected raffinate and extract throughput were then extrapolated from this amount.

Acetone insolubles were determined according to Lange R., Fiebig H. J. (1999): Separation of Phospholipids, Standard Methods of DGF, Fett/Lipid 101: 77-79.

This method is based on the solubility of lecithin components such as triglycerides, fatty acids, sterols, and other acetone-soluble components, and the insolubility of the phospholipids and glycophospholipids in acetone under the test conditions. The latter are termed acetone insolubles (AI).

Generally, about 5 g of a lecithin sample is repeatedly vigorously mixed with about 40 ml of acetone of 0° C. Acetone soluble components are dissolved, while insoluble components precipitate. The precipitates are then filtered off, and washed with acetone, and the residue is dried. The method is repeated at least 4 times, or until no soluble components are detected in the acetone. The amount of the combined residues is considered as the acetone insoluble part of the lecithin sample, and the weight percentage is calculated, by subtracting the content of acetone-soluble components and the water content.

Compositional Data:

An aliquot of the well homogenised extract and raffinate, respectively, were weighed into a round bottom flask of known weight. The solvent was removed in a rotary evaporator at 50-60° C. and reduced pressure, automatically adjusting pressure according to vapour pressure. A final drying step was performed in a freeze-dryer until constant weight was achieved. Dry mass and total yield were calculated from the corrected throughput and dry mass.

Chemical Composition:

Dried samples of extract, with residual raffinate content removed, and of the raffinate phase were analysed for their AI content and acid value. The phospholipid composition was determined using a liquid-chromatographic method.

The identification and quantification of the various phospholipid components may conveniently be executed by different methods, including thin-layer chromatography (TLC), high performance liquid chromatography (HPLC) and $^{31}P$ nuclear magnetic resonance spectroscopy ($^{31}P$-NMR) for the phospholipids only. Suitable methods are disclosed in London E., Feigenson G. W. (1979): Phosphorous NMR Analysis of Phospholipids in Detergents, J. Lipid Res. 20: 408-412; Aitzetmüller K. (1984): HPLC and Phospholipids, Part I: General Considerations, Fette, Seifen, Anstrichm. 86: 318-322; and Aloisi J. D., Sherma J., Fried B. (1990): Comparison of Mobile Phases for Separation and Quantification of Lipids by One-Dimensional TLC and Preadsorbent High Performance Silica Gel Plates, J. Liq. Chromatogr. 13:3949-3961.

Examples 1 to 8

Crude soya lecithin was extracted with ethanol, comprising 2.5% wt. and 4.5% wt. water, respectively. Table 1 depicts the conditions that were applied results of various runs:

TABLE 1

Applied conditions

| Ex. | Extract. stages | T [°] | Water in Ethanol [%] | Extraction Ratio Extractant to Raffinate | Rotation speed |
|---|---|---|---|---|---|
| 1 | 4 | 30 | 4.5 | 1 | 2900 |
| 2 | 4 | 30 | 4.5 | 1 | 2300 |
| 3 | 6 | 12 | 4.5 | 1 | 2300 |
| 4 | 6 | 12 | 4.5 | 1 | 2900 |
| 5 | 6 | 12 | 2.5 | 2 | 2300 |
| 6 | 6 | 12 | 2.5 | 2 | 2900 |
| 7 | 4 | 12 | 2.5 | 1 | 2900 |
| 8 | 4 | 12 | 2.5 | 1 | 2300 |

The obtained extract and raffinate phases were dried to remove volatiles extractant and water, and analysed for acetone insolubles, acid value and composition (see Table 2). The extraction ratio refers to the weight ratio of extractant and raffinate employed in each stage.

TABLE 2

Dried extract and raffinate composition

| | Dried Extract | | | Dried Raffinate (ISOL) | | | | | |
|---|---|---|---|---|---|---|---|---|---|
| Ex. | % AI | % PC | Acid Value | % AI | % PA | % PC | % PE | % PI | Acid Value |
| 1 | 58.7 | 40.9 | 16.6 | 66.8 | 5.3 | 8.0 | 18.6 | 15.9 | 21.2 |
| 2 | 54.2 | 39.5 | 18.4 | 66.1 | 4.6 | 13.2 | 16.9 | 12.4 | 19.5 |
| 3 | 57.5 | 41.1 | 17.6 | 66.4 | 5.0 | 9.2 | 17.5 | 14.6 | 20.7 |
| 4 | 56.4 | 39.3 | 17.2 | 66.7 | 5.0 | 8.6 | 17.8 | 13.2 | 20.5 |
| 5 | 53.4 | 35.2 | 16.5 | 68.1 | 5.2 | 9.2 | 18 | 14.2 | 20.8 |
| 6 | 54.1 | 34.7 | 15.7 | 68.7 | 5.4 | 6.5 | 18.7 | 14.4 | 21.7 |
| 7 | 53 | 36 | 16.9 | 66.9 | 4.8 | 12.8 | 18.6 | 12.8 | 20.1 |
| 8 | 51.5 | 37.8 | 17.4 | 67.1 | 4.7 | 12.8 | 17.5 | 12.3 | 20.1 |

The examples illustrate that using multistage countercurrent centrifugal extraction process, it is possible to achieve yields of up to 40% of an ethanol soluble fraction of lecithin showing a high PC content and an adequate PC/AI ratio.

The corresponding raffinate phase is strongly depleted in PC, and has a composition that would typically only be achieved from performing single stage ethanol extraction of previously de-oiled lecithin.

The obtained raffinate fractions were found in particular useful as emulsifiers for food products. In the experiments, it was found that a higher extraction ratio, i.e. extract to raffinate ratio increased the AI content in the raffinate. Higher ethanol temperature also led to increased AI in raffinate, as did a lower water concentration in the ethanol. Both factors appear to enhance triglyceride extraction with the ethanol. While the PC content in raffinate could be reduced by applying a higher extraction ratio, this was also obtained from higher temperature, more extraction stages and increased rotor speed.

Further, a higher extraction ratio, higher temperature and a reduction of the water content in the ethanol also lead to an increase of PA, PI and PE concentrations in the raffinate.

Higher water concentration and higher temperature of the ethanol were found to increase the PC content in the extract, while increasing the extraction ratio led to a lower PC content in the extract.

Examples 9 and 10

Preparation of Emulsions

A commercially available acetone-deoiled and fractionated emulsifier derived from soy lecithin (comparative example 9) was compared to an emulsifier according to the invention (Example 10), which was derived from a multi-stage counter-flow extraction of crude soy lecithin with Ethanol, and not subjected to a deoiling with acetone. The composition of the two emulsifier is shown in Table 3:

TABLE 3

| Emulsifier composition | | |
|---|---|---|
| [%] weight | Comparative Example 9 | Example 10 |
| AI | 61.2 | 65.4 |
| PC | 5.0 | 10.1 |
| LPC | 0.5 | — |
| PE | 13.0 | 9.8 |
| LPE | 0.6 | — |
| PI | 13.7 | 9.6 |
| PA | 5.2 | 3.4 |
| LPA | 0.4 | — |
| PS | 0.5 | — |
| $R_1$ | 1.7 | 2.3 |
| $R_2$ | 1.0 | 1.5 |

The two emulsifiers were formulated into a primary emulsion with the following composition, applying 2% AI as calculated based on the analytical value acetone insoluble (AI), see formula III:

$$m_{lecithin}[\%] = \frac{2\% * 100\%}{AI_{Lecithin}[\%]} \quad \text{(III)}$$

The primary emulsions were then employed as replacement for oil in a salad dressing composition, with the following composition (table 4):

TABLE 4

| INGREDIENTS | % |
|---|---|
| Water | 13.92 |
| Sugar | 3.0 |
| Salt | 2.0 |
| Potassium Sorbate | 0.12 |
| EDTA | 0.01 |
| Xanthan Gum | 0.20 |
| Emulsions Ex. 9/10 | 70.00 |
| Egg yolk powder | 3.50 |
| Vinegar 7° | 5.0 |
| Mustard | 2.0 |

The sugar, salt, and preservative was added to the water at room temperature and mixed thoroughly. The composition was poured into a colloid mill. The xanthan gum was added to a small part of the emulsions Ex. 9 and 10, and blended until a smooth product was obtained (the dispersion phase).

The dispersion phase and the water phase were emulsified for 30 seconds, then the emulsion as allowed to rest for 5 minutes.

Then the primary emulsions derived from Example 9 and 10 were added to the colloid mill. After ⅔ of these were added, the vinegar and mustard were added. The entire composition was emulsified further for 30 seconds, and filled into jars at room temperature.

The resulting secondary dispersion according to the invention showed a smaller particle size, and a stronger stability as compared to the comparative example. The water-in-oil-in water emulsion according to the invention tested are characterized by having good levels of stability as evidenced by data showing no separation for a period of time up to 72 hours.

The invention claimed is:

1. A phospholipid emulsifier composition comprising Phosphatidyl Choline (PC), Lyso Phosphatidyl Choline (ITC), Phosphatidyl Inositol (PI), Phosphatidyl Ethanolamine (PE) and Phosphatidic Acid (PA), and having a phospholipid ratio $R_1:R_2$ in the range of from 1:1 to 1.7:1,
wherein $R_1$ is defined as a weight ratio of phospholipid components according to general formula I:

$$R_1 = \frac{PC + LPC + PI + PA}{PE}, \quad \text{(I)}$$

and wherein $R_2$ is defined as a weight ratio of phospholipid components according to general formula II:

$$R_2 = \frac{PC + LPC + PI}{PE + PA}. \quad \text{(II)}$$

2. An emulsifier according to claim 1, having an Acetone Insoluble content of at least 60 weight %, and a Phosphatidyl Choline content of at most 20 weight %.

3. A water-in-oil emulsion comprising the emulsifier composition of claim 1.

4. A water-in-oil-in-water emulsion comprising an emulsion according to claim 3.

5. An emulsion according to claim 3, further comprising one or more texturing agents, and/or a calcium salt.

6. A counter-current extraction process for the preparation of the emulsifier according to claim 1, comprising:
   (a) contacting a phospholipid-containing starting material under agitation with an extractant comprising an aliphatic alcohol selected from $C_1$ to $C_3$ alcohols and combinations thereof for a period of time sufficient to effectuate the transfer of at least a fraction of phospholipids in the phospholipid-containing starting material into the extractant to obtain a mixture;
   (b) separating the obtained mixture into a phospholipid-enriched extract from a residual raffinate by a process comprising applying centrifugal forces, wherein the phospholipid-enriched extract from each separation stage is at least in part returned to a previous, or further upstream mixing stages, and wherein a final phospholipid-enriched extract comprising the emulsifier is separated from a first residual raffinate, and
   (c) isolating at least part of the phospholipids from the raffinate to obtain the emulsifier.

7. A process according to claim 6, wherein in step (a) the phospholipid-containing starting material is contacted with the extractant in a co-current or counter-current mixing operation.

8. A process according to claim 6, wherein in the aliphatic alcohol has a water concentration in the range of from 0 to 10% by weight.

9. A process according to claim 6, wherein steps (a) and (b) are executed at least in part in a multistage extraction apparatus comprising for each stage:
   i) a rotor, ii) a mixing chamber connected to the rotor, and wherein two liquid streams are mixed, and wherein the mixing chamber comprises iia) a stationary agitator placed in the mixing chamber, and iib) a settling chamber in which the liquid streams are separated by centrifugal force generated by the mixing chamber.

10. A process according to claim 9, wherein the stationary agitator comprises a stationary disc, and wherein mixing is achieved through speed differentials between the stationary disc and the rotating mixing chamber.

11. The process according to claim 6, wherein the phospholipid-containing starting material comprises lecithin, selected from the group consisting of soybean lecithin, corn lecithin, rapeseed lecithin, rice oil lecithin, sunflower lecithin, cotton seed lecithin, palm oil lecithin, marine oil lecithin, biomass lecithin, peanut lecithin, egg yolk lecithin, milk lecithin and/or brain lecithin.

12. The process according to claim 6, further comprising isolating at least part of the phospholipids from the raffinate and/or extract phase.

13. A process for the preparation of an water-in-oil emulsion, comprising (i) contacting a lipid composition with a suitable amount of an emulsifier according to claim 1 to obtain an emulsion stabilized lipid composition, and (ii) contacting the emulsion stabilized lipid composition with an first aqueous phase to form a water-in-oil emulsion.

14. A process according to claim 13, further comprising dispersing the water-in oil emulsion in a second aqueous phase to obtain an oil-in-water-in oil emulsion.

15. A process according to claim 14, wherein the oil-in-water-in oil emulsion is prepared using a cross-flow membrane with suitable pore size.

16. An emulsifier according to claim 2, wherein the Phosphatidyl Choline content is at most 12 weight %.

17. A process according to claim 6, wherein the aliphatic alcohol has a water concentration in the range of from 0 to 5% by weight.

* * * * *